US012678532B2

(12) United States Patent
Abbas et al.

(10) Patent No.: US 12,678,532 B2
(45) Date of Patent: Jul. 14, 2026

(54) ABSORBENT ARTICLE COMPRISING A LUBRICANT AGENT

(71) Applicant: Essity Hygiene and Health Aktiebolag, Gothenburg (SE)

(72) Inventors: Shabira Abbas, Gothenburg (SE); Charlotte Persson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 885 days.

(21) Appl. No.: 17/784,285

(22) PCT Filed: Dec. 12, 2019

(86) PCT No.: PCT/EP2019/084952
§ 371 (c)(1),
(2) Date: Jun. 10, 2022

(87) PCT Pub. No.: WO2021/115607
PCT Pub. Date: Jun. 17, 2021

(65) Prior Publication Data
US 2023/0039049 A1     Feb. 9, 2023

(51) Int. Cl.
*A61L 15/50* (2006.01)
*A61L 15/34* (2006.01)
*A61L 15/48* (2006.01)

(52) U.S. Cl.
CPC .............. *A61L 15/50* (2013.01); *A61L 15/34* (2013.01); *A61L 15/48* (2013.01); *A61L 2420/06* (2013.01)

(58) Field of Classification Search
CPC .......... A61L 15/50; A61L 15/34; A61L 15/48; A61L 2420/06
See application file for complete search history.

(56) References Cited

U.S. PATENT DOCUMENTS

| | | | | |
|---|---|---|---|---|
| 5,554,243 A | * | 9/1996 | Igaue | A61F 13/531 |
| | | | | 156/324 |
| 5,665,083 A | * | 9/1997 | Igaue | A61F 13/531 |
| | | | | 428/137 |
| 6,245,051 B1 | * | 6/2001 | Zenker | A61F 13/5376 |
| | | | | 604/385.23 |
| 6,437,214 B1 | * | 8/2002 | Everett | A61F 13/5376 |
| | | | | 604/378 |
| 2002/0128621 A1 | | 9/2002 | Kruchoski et al. | |
| 2003/0114520 A1 | * | 6/2003 | Pereira | A61K 8/86 |
| | | | | 514/532 |
| 2004/0116018 A1 | | 6/2004 | Fenwick et al. | |
| 2004/0175403 A1 | | 9/2004 | Lukenbach et al. | |
| 2004/0242097 A1 | | 12/2004 | Hasenoehrl et al. | |
| 2005/0282456 A1 | | 12/2005 | Zhao et al. | |
| 2007/0003993 A1 | | 1/2007 | Kritzman et al. | |
| 2007/0009676 A1 | | 1/2007 | Tamagawa et al. | |
| 2007/0043330 A1 | * | 2/2007 | Lankhof | A61F 13/51394 |
| | | | | 604/378 |

| | | | | |
|---|---|---|---|---|
| 2009/0137975 A1 | * | 5/2009 | Kohira | D04H 3/11 |
| | | | | 604/385.01 |
| 2011/0118686 A1 | * | 5/2011 | Vega | A61F 13/8405 |
| | | | | 560/190 |
| 2011/0263760 A1 | * | 10/2011 | Jakupca | C08G 79/04 |
| | | | | 558/158 |
| 2011/0282312 A1 | | 11/2011 | Turner et al. | |
| 2013/0046263 A1 | * | 2/2013 | Fukudome | B32B 5/022 |
| | | | | 604/375 |
| 2013/0071535 A1 | * | 3/2013 | Fenyvesi | A61K 36/02 |
| | | | | 426/534 |
| 2013/0345346 A1 | * | 12/2013 | Jakupca | C08G 65/3353 |
| | | | | 558/87 |
| 2014/0005622 A1 | * | 1/2014 | Wirtz | A61F 13/539 |
| | | | | 604/366 |
| 2014/0005623 A1 | * | 1/2014 | Wirtz | A61F 13/53418 |
| | | | | 604/366 |
| 2014/0163500 A1 | * | 6/2014 | Roe | A61F 13/49001 |
| | | | | 604/374 |

(Continued)

FOREIGN PATENT DOCUMENTS

| | | |
|---|---|---|
| CN | 114222553 A | 3/2022 |
| CO | 2017007321 A2 | 9/2017 |

(Continued)

OTHER PUBLICATIONS

International Preliminary Report on Patentability and Written Opinion of the International Searching Authority (Forms PCT/IB/326, PCT/IB/373 and PCT/ISA/237) issued on Jun. 23, 2022, by the International Bureau of WIPO, in corresponding International Application No. PCT/EP2019/084952. (7 pages).
Office Action (Notification of the First Office Action) issued on Jul. 12, 2022, by the Chinese Patent Office in corresponding Chinese Patent Application No. 201980101691.5, and an English Translation of the Office Action. (20 pages).
Office Action issued on Nov. 27, 2024, by the Canadian Patent Office in corresponding Canadian Patent Application No. 3,157,951. (4 pages).

(Continued)

*Primary Examiner* — Guy K Townsend
(74) *Attorney, Agent, or Firm* — BUCHANAN INGERSOLL & ROONEY PC

(57) ABSTRACT

The present disclosure relates to an absorbent article, such as an infant diaper, training pant, feminine hygiene article, adult incontinence article or wound care dressing. The absorbent article comprises a topsheet. The topsheet comprises or consists of a fibrous nonwoven layer arranged on a wearer facing side of the topsheet. The fibrous nonwoven layer is coated over a coated area on the wearer facing side of the topsheet with a coating composition. The coating composition comprises a lubricant agent comprising an alkoxylated diester selected from the group consisting of fatty ester lubricants.

17 Claims, No Drawings

(56) References Cited

U.S. PATENT DOCUMENTS

| | | | |
|---|---|---|---|
| 2014/0163501 A1* | 6/2014 | Ehrnsperger | A61F 13/49 604/374 |
| 2014/0163506 A1* | 6/2014 | Roe | A61F 13/535 604/378 |
| 2014/0163511 A1* | 6/2014 | Roe | A61F 13/532 604/385.101 |
| 2014/0303582 A1* | 10/2014 | Wright | A61F 13/15658 156/60 |
| 2014/0329943 A1* | 11/2014 | Jakupca | C08L 85/02 558/156 |
| 2014/0378590 A1* | 12/2014 | Jakupca | C08G 65/3353 558/87 |
| 2015/0005727 A1* | 1/2015 | Matsushita | A61L 15/26 442/382 |
| 2015/0065976 A1* | 3/2015 | Roe | A61F 13/42 604/374 |
| 2015/0080821 A1* | 3/2015 | Peri | C08J 3/245 604/385.01 |
| 2015/0203636 A1* | 7/2015 | Jakupca | C08L 23/12 558/87 |
| 2016/0002384 A1* | 1/2016 | Nacharaju | A61Q 5/06 525/132 |
| 2016/0136321 A1* | 5/2016 | Chmielewski | A61F 13/513 427/365 |
| 2016/0243259 A1* | 8/2016 | Almarsson | A61K 38/00 |
| 2016/0270982 A1* | 9/2016 | Raycheck | A61F 13/55105 |
| 2016/0354260 A1* | 12/2016 | Roe | A61F 13/532 |
| 2016/0376263 A1* | 12/2016 | Patron | A61K 8/4973 514/784 |
| 2017/0087199 A1* | 3/2017 | Patron | A61K 31/381 |
| 2017/0096418 A1* | 4/2017 | Patron | A23L 33/10 |
| 2017/0156947 A1* | 6/2017 | Esquerra | A61F 13/496 |
| 2017/0157021 A1* | 6/2017 | Traynor | A61K 8/466 |
| 2017/0216164 A1* | 8/2017 | Traynor | A61K 8/895 |
| 2017/0216165 A1* | 8/2017 | Traynor | A01N 25/28 |
| 2017/0281425 A1* | 10/2017 | Herfert | A61F 13/535 |
| 2017/0312149 A1* | 11/2017 | Bianchi | A61F 13/537 |
| 2018/0028372 A1 | 2/2018 | Fernkvist et al. | |
| 2018/0168874 A1 | 6/2018 | Gary et al. | |
| 2019/0015304 A1* | 1/2019 | Musa | A61K 8/06 |
| 2019/0192354 A1* | 6/2019 | Bewick-Sonntag | A61F 13/47 |
| 2019/0290940 A1* | 9/2019 | Traynor | A61Q 19/00 |
| 2019/0375875 A1* | 12/2019 | Musa | A61K 8/817 |
| 2019/0382519 A1* | 12/2019 | Musa | A61K 8/06 |
| 2020/0000693 A1* | 1/2020 | Traynor | A61K 47/02 |
| 2020/0170854 A1 | 6/2020 | Husmark et al. | |
| 2020/0330292 A1 | 10/2020 | Maschino et al. | |
| 2021/0169709 A1* | 6/2021 | Bauer | A61L 15/24 |
| 2022/0096282 A1 | 3/2022 | Blomström et al. | |
| 2022/0287944 A1* | 9/2022 | Costache | A61K 8/64 |
| 2022/0323269 A1* | 10/2022 | Burn Lees | A61L 15/28 |
| 2023/0157907 A1 | 5/2023 | Rönnberg et al. | |

FOREIGN PATENT DOCUMENTS

| | | | |
|---|---|---|---|
| CO | 2021008560 | A2 | 7/2021 |
| CO | 2022016625 | A2 | 11/2022 |
| EP | 1371379 | A1 | 12/2003 |
| JP | 2003261631 | A | 9/2003 |
| JP | 2004149679 | A | 5/2004 |
| JP | 2005511493 | A | 4/2005 |
| WO | 9855158 | A2 | 12/1998 |
| WO | 0019972 | A1 | 4/2000 |
| WO | 0078846 | A1 | 12/2000 |
| WO | 02051363 | A2 | 7/2002 |
| WO | 03013439 | A2 | 2/2003 |
| WO | 03105916 | A1 | 12/2003 |
| WO | 2007060649 | A2 | 5/2007 |
| WO | 2007070643 | A2 | 6/2007 |
| WO | 2008137298 | A1 | 11/2008 |
| WO | 2016114692 | A1 | 7/2016 |
| WO | 2018004400 | A1 | 1/2018 |
| WO | 2019185113 | A1 | 10/2019 |
| WO | 2021028415 | A1 | 2/2021 |
| WO | 2021115607 | A1 | 6/2021 |

OTHER PUBLICATIONS

Office Action (Notice of Reasons for Refusal) issued on Apr. 17, 2023, in corresponding Japanese Patent Application No. 2022-535651 and English translation of the Office Action. (15 pages).

Office Action/Examination Search Report issued on Aug. 17, 2023, in corresponding Canadian Patent Application No. 3,157,951. (4 pages).

Office Action (Decision of Rejection) issued on Nov. 6, 2023, in corresponding Japanese Patent Application No. 2022-535651 and English translation of the Office Action. (7 pages).

Griffin, William C., "Calculation of HLB Values of Non-Ionic Surfactants", Journal of the Society of Cosmetic Chemists, presented May 14, 1954, pp. 249-256, vol. 5, No. 4, Atlas Powder Company, Wilmington, Delaware. (8 pages).

International Search Report (PCT/ISA/210) and Written Opinion (PCT/ISA/237) mailed on Jul. 3, 2020, by the European Patent Office as the International Searching Authority for International Application No. PCT/EP2019/084952. (9 pages).

Huang, "Method for Producing Chemical Commodities", Hunan Science and Technology Press, Apr. 1990, First Edition. (9 pages).

Office Action (Decision of Rejection) issued on Mar. 22, 2023, by the Chinese Patent Office in corresponding Chinese Patent Application No. 201980101691.5, and an English Translation of the Office Action. (16 pages).

Office Action (Substantive Examination Adverse Report) issued on Mar. 24, 2023, by the Malaysian Patent Office in corresponding Malaysian Patent Application No. PI2022002293. (3 pages).

"Cromollient SCE", Croda Inc., published May 2017. (29 pages).

"Innovative Finishes & Processing Aids for Nonwovens Applications", Croda, Inc., published Feb. 2017. (5 pages).

Office Action (Communication of a Notice of Opposition) issued on Mar. 27, 2025, by the European Patent Office in corresponding European Patent Application No. 19831619.2. (35 pages).

Office Action issued on Mar. 14, 2025, by the Colombian Patent Office in corresponding Colombian Patent Application No. NC2022/0008077, and an English Translation of the Office Action. (22 pages).

Office Action issued on Aug. 27, 2025, by the Colombian Patent Office in corresponding Colombian Patent Application No. NC2022/0008077, and an English Translation of the Office Action. (36 pages).

* cited by examiner

ABSORBENT ARTICLE COMPRISING A LUBRICANT AGENT

TECHNICAL FIELD

The present disclosure pertains to an absorbent article such as an infant diaper, training pant, feminine hygiene article, adult incontinence article and wound care dressing. In particular this disclosure pertains to an absorbent article comprising a topsheet being coated with a lubricant agent.

BACKGROUND OF THE INVENTION

Absorbent articles of the kind to which this disclosure relates are worn against the skin with the topsheet facing the skin of the user. All uses of products which are applied in direct contact with the skin may lead to unwanted side-effects. These may occur as a result of occlusion, moisture and mechanical factors, such as friction, between the skin and the absorbent article. These factors which all, to different degrees, interact and amplify the influence of each other may cause different forms of skin irritation to users of said articles. While the body facing material is made of a soft, compliant material, the material rubs against the skin during use and may leave a skin which is not completely dry and free of the bodily fluids. After wetting the mechanical friction, especially so-called wet-friction, between the material and the skin may thus increase the risk of skin irritation.

When using absorbent articles, friction occurs between the skin and the surface of the absorbent article, for example a nonwoven material. The friction between the nonwoven material and skin in presence of moisture/liquid is complex and even a very small amount of moisture has a negative impact on the friction, so-called wet friction. Creams, lotions, or ointments can be used to reduce the friction and to improve the skin condition. However, the use of such hydrophobic compositions has a negative impact on the absorbency performance of absorbent articles, and it is not always desired to transfer substances and composition to the skin of the user. Surface materials of absorbent articles may also be provided with surfactants to increase the liquid inlet into the absorbent article. However, while providing the absorbent articles with absorbency benefits, surfactants may cause skin irritations to users having sensitive skin.

As mentioned above, one reason for mechanical discomfort is relating to clinging, i.e. the forces acting between the absorbent product and the human skin in the presence of small amounts of moisture such as perspiration, sweat and urine. Clinging can be described as a perpendicular force acting between a solid material and a support surface in the presence of a small amount of moist. Wet friction is experienced between a wet or moist product and skin. Wet friction can occur even at small concentrations of moist or liquid presence in the product or in the boundary between the nonwoven and the skin. Dry friction is experienced between a dry product and skin.

It is an object of the present invention to provide an absorbent article having improved skin benefits and absorbency performance, over a prolonged period of use and after larger wettings.

SUMMARY

One or more of the above objects may be achieved with an absorbent article in accordance with claim 1. Further advantages and advantageous features of the invention are disclosed in the following description and in the dependent claims.

The absorbent article, such as an infant diaper, training pant, feminine hygiene article, adult incontinence article and wound care dressing, as disclosed herein comprises a topsheet. The topsheet comprises or consists of a fibrous nonwoven layer arranged on a wearer facing side of the topsheet. The fibrous nonwoven layer is coated over a coated area on the wearer facing side of the topsheet with a coating composition. The coating composition comprises a lubricant agent comprising an alkoxylated diester selected from the group consisting of fatty ester lubricants.

The topsheet of the absorbent article is the layer facing the wearer during use. The fibrous nonwoven layer and the topsheet may consist essentially of thermoplastic polymeric fibers. Optionally, the thermoplastic polymeric fibers are selected from polyolefins, such as polypropylene and/or polyethylene and blends and combinations thereof.

To provide the topsheet of an absorbent article with a lubricant agent comprising an alkoxylated diester selected from the group consisting of fatty ester lubricants has been found by the present inventors to provide a surprisingly reduced wet friction between the wearer-facing topsheet and the skin of the user. The most surprising effect of the lubricant has thus been seen under wet, or moist conditions, however the lubricant agent according to the present disclosure shows a reduced friction both under dry and wet conditions. A low friction between the wearer-facing surface layer and the skin decreases the risk for chafing of the skin against the napkin which otherwise may lead to skin irritation and itchiness.

The alkoxylated diester may be an alkoxylated diester of myristyl alcohol and adipic acid, which is a multifunctional emollient which has been found by the present inventors to provide the topsheet with a surprisingly low wet friction and a silky feel against the skin.

The coating composition may comprise one or more surfactant(s) such as one or more cationic surfactants or one or more anionic surfactants, one or more non-ionic or zwitterionic surfactants or a combination of surfactants. The use of surfactants on topsheets for absorbent articles is well-known for increasing the liquid inlet and improving the absorbency performance of the absorbent article. Surfactants, in particular cationic and/or anionic surfactants, may cause skin irritations when being used in contact with the skin. However, it has now been found that a composition comprising one or more surfactants, such as cationic and/or anionic surfactants in combination with a lubricant agent in accordance with the present disclosure can mitigate the irritation from the surfactants and provide a silky soft feeling to the topsheet, both prior to and after repeated wettings of the absorbent article. Surfactants included in the coating composition in combination with the lubricant agent may furthermore be surfactants having lower molecular weights, such as surfactants having a molecular weight from 1000 g/mole and below. Such surfactants may be quicker to reduce the surface tension of the topsheet material but may be more prone to migrate from the topsheet to the skin and thereby cause skin irritations. However, when combining such surfactants with the lubricant agent in the coating composition the lubricant agent may retain the surfactants on the absorbent article and the risk of the surfactant migrating to the skin may be reduced.

The composition may comprise from 50% by weight to 95% by weight of the lubricating agent and from 5% by weight to 50% by weight of the one or more surfactant(s).

The coating composition may be applied by several different methods, such as for example spraying, kiss rolling or dipping. For application methods in which the lubricant needs to be mixed with water to prior to application, the lubricant may have an HLB which is within the range of from 6 to 18 in order to mix well with water, preferably within the range of from 10 to 18.

By "HLB" herein is meant the hydrophilic-lipophilic balance. As is known to the person skilled in the art, the HLB of a compound is a measure of the degree to which it is lipophilic or hydrophilic. The HLB value may be determined by calculating values for the different regions of the compound. One method to determine the HLB value is Griffin's method, as described in 1954, *Journal of the Society of Cosmetic Chemists,* 5 (4): 249-56.

The lubricant agent may have a molecular weight of 500 g/mol or more or such as 1000 g/mol or more. The lubricant agent may have a molecular weight of up to 100 000 g/mol, or up to 60 000 g/mol. A lubricant agent having a molecular weight of 500 g/mol or more, or 1000 g/mol or more, is less prone to migrate from the fibrous nonwoven and to the skin of the user and/or downwards into the absorbent articles, such as into an underlying absorbent core. This thus prolongs the effect of the lubricant agent on the wearer facing side of the absorbent article. Furthermore, as the lubricant agent may have a molecular weight of 500 g/mol or more, or 1000 g/mol or more, it does not pass the skin barrier if a fraction of the lubricant agent would anyhow migrate from the fibrous nonwoven and to the skin of the user.

When the composition additionally comprises one or more surfactant(s), a lubricant agent having a molecular weight of 500 g/mol or more, may retain compounds such as surfactant on the fibrous nonwoven due to its larger molecular weight. Hence, besides prolonging the effect of the surfactant(s) it also prevents that the one or more surfactants migrates to the skin which may otherwise cause skin irritations.

The coating may have a water content of 0.5 wt. % or less, such as 0.1 wt. % or less. The coating according to the present disclosure may be a dry coating, having a water content of 0.5 wt. % or less, such as 0.1 wt. % or less. The coating provided on the fibrous nonwoven of the topsheet is intended to remain on the topsheet throughout the use of the absorbent article and a dry coating remains to a higher extent on a topsheet than liquid or semi-liquid compositions which may be more prone to migrate from the topsheet. The fact that the coating is a dry coating has been seen to provide a maintained wet friction reducing effect over time, such that the wet friction reducing effect is kept after multiple wettings and over an extended period of time.

The fibrous nonwoven layer may comprise from 0.1 wt. % of the coating composition, as measured over the total coated area, i.e. the nonwoven being coated by the coating composition. Optionally, the fibrous nonwoven layer may comprise from 0.3 wt. %, or 0.5 wt. %, of the coating composition, as measured over the total coated area. The fibrous nonwoven layer may comprise from 1 wt. % or from 2 wt. % and up to 10 wt. %, or up to 8 wt. %. Such coating levels have been seen to provide an improved wet friction.

The coated area may be at least 25%, such as 30% of the total surface area of the topsheet.

The coating composition may include a buffering system, such as a dermatologically acceptable acid and a salt thereof, and both are present in amounts providing together a pH buffering capacity. Due to the acid/buffer content, natural skin pH can be stabilized. The pH of healthy skin lies in the range between 4.5 and 6.0. This slightly acidic pH is caused by the acid mantle of the human skin. The acid mantle of the human skin is a very fine, slightly acidic film on the surface of the skin acting as a barrier to the bacteria, viruses and other potential contaminants that might penetrate the skin. Accordingly, it is important to minimize the impact of external factors on skin pH. The buffering system may be selected from (i) inorganic acids such as boric acid; (ii) optionally hydroxylated, organic acids having 2 to 24 carbon atoms, optionally hydroxylated, organic acids having 3 to 6 carbon atoms, or optionally citric acid, lactice acide, isoascorbic acid, or combinations thereof; and (iii) polymeric organic acids such as polyacrylic acid, and combinations thereof. The optionally present salt thereof is the salt corresponding to the selected acid.

The topsheet may in its transverse direction have a first and a second longitudinal side portion and an intermediate portion located between the first and the second longitudinal side portion. The first and the second longitudinal side portion may each have a width of 30% of the width of the topsheet and the intermediate portion may have a width of 40% of the topsheet, as measured at the widest point of the topsheet, and wherein the intermediate portion may be continuously coated with the coating composition.

The absorbent article may comprise a backsheet and an absorbent core arranged between the topsheet and the backsheet. The backsheet may be a breathable or non-breathable backsheet.

The coated area may cover from 40% to 100% of the underlying absorbent core, such as from 60% to 100% of the underlying absorbent core.

Non-breathable backsheets may be less expensive and less resource demanding to produce, in particular when the breathability is due to the use of filler particles in plastic sheets of material with a subsequently stretching step. When a non-breathable backsheet is used in absorbent articles the level of moist in the article increases as there is less ventilation of the absorbent article. However, when using the coating composition according to the present disclosure a surprisingly reduced wet friction is achieved despite of the backsheet being non-breathable.

The absorbent core may comprise pulp fibers.

A risk when providing a coating on the topsheet of an absorbent article is that the coating, particularly when being exposed to liquid, migrates down into the absorbent article, in this case resulting in a reduced friction lowering effect. It has however been found that when using an absorbent core comprising pulp fibers, such as in the range of from 30 wt. % or more, or from 40 wt. %, or from 45 wt. % or more, the coating is less prone to migrate down from the topsheet layer, even during multiple wettings. It is believed to be due to the affinity of the lubricant agent being higher for thermoplastic hydrophobic fibers, such as the type of fibers mainly used in fibrous nonwoven material than the affinity for the lubricant agent to pulp fibers.

The absorbent article may include a front waist region and a rear waist region.

The absorbent article may be an over-night absorbent article, a pant diaper, an open diaper or a belted absorbent article.

Absorbent articles such as belted absorbent article, open diapers and pant diapers, i.e. absorbent articles having a front and rear waist region, all covers relatively large areas of the lower torso and may create occlusion for certain parts of the skin, thereby potentially including overhydration of the skin. Such articles may particularly benefit from being provided with the coating composition according to the present disclosure.

The absorbent article may be an over-night absorbent article.

DETAILED DESCRIPTION

The term "absorbent articles" refers to products that are placed against the skin of the wearer to absorb and contain body exudates, like urine, faeces and menstrual fluid. The disclosure mainly refers to disposable absorbent articles, which means articles that are not intended to be laundered or otherwise restored or reused as an absorbent article. Examples of disposable absorbent articles include feminine hygiene products such as sanitary napkins and panty liners, incontinence pads and diapers and the like. Absorbent articles may also refer to wound dressings. A wound dressing is an article used by a person for application to a wound to promote healing and/or prevent further harm. A dressing is designed to be in direct contact with the wound, which makes it different from a bandage, which is primarily used to hold a dressing in place.

The topsheet may include or consist of fibrous nonwoven layer(s) being spunbonded, meltblown, carded, hydroentangled, wetlaid etc. Suitable nonwoven materials can be composed of natural fibers, such as woodpulp or cotton fibres, synthetic thermoplastic fibres, such as polyolefins, polyesters, polyamides and blends and combinations thereof or from a mixture of natural and synthetic fibres. The materials suited as topsheet materials should be soft and non-irritating to the skin and be readily penetrated by body fluid, such as urine or menstrual fluid. The topsheet material may essentially consist of synthetic thermoplastic fibers, such as polyolefins, polyesters, polyamides and blends and combinations thereof. The synthetic fibers may be mono-component fibers, bicomponent fibers or multicomponent fibers including polyesters, polyamides and/or polyolefins such as polypropylene and polyethylene.

That the topsheet and the fibrous nonwoven layer may "essentially consist" of thermoplastic synthetic fibers means that at least 95% of the fibers are thermoplastic synthetic fibers, such as at least 99%, such as at least 100% of the fibers in the nonwoven material are non-absorbent fibers. The topsheet material and the fibrous material may however also include further substances present in small amounts, such as for example binders and pigments, as known by the person skilled in the art.

The absorbent core may be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's sanitary articles, often comprise a compressed mixed or layered structure of cellulosic fluff pulp and superabsorbent. The size and absorbent capacity of the absorbent structure may be varied to be suited for different uses such as sanitary articles, pantyliners, adult incontinence pads and diapers, baby diapers, pant diapers, etc.

The backsheet may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. The backsheet material can be breathable, allowing vapor to escape from the absorbent structure, while still preventing liquids from passing through the backsheet material. The backsheet material may alternatively be non-breathable.

The absorbent article may be produced by preparing an aqueous solution comprising a lubricant agent comprising an alkoxylated diester selected from the group consisting of fatty ester lubricants. The composition may comprise the lubricant in a concentration of from 0.1 to 100 wt % of the aqueous solution. The aqueous solution may optionally include one or more surfactant(s), such as in a in a concentration of from 5 to 50 wt % of the aqueous solution. The surfactant(s) may be non-ionic, zwitterionic, cationic or anionic surfactant or any combinations thereof.

The aqueous solution may be applied to the fibrous nonwoven layer for example by spraying, coating or soaking the fibrous nonwoven layer in the aqueous solution. The aqueous solution may be applied to the fibrous nonwoven layer after assembly of the absorbent article or to the fibrous nonwoven web material prior to cutting of the web material and assembly of the absorbent article.

After applying the solution to the fibrous nonwoven layer, the fibrous nonwoven layer is dried to provide a dry coating on the fibrous nonwoven layer having a water content of 0.5 wt. % or less, or 0.1 wt. % or less.

The aqueous solution may be applied so that the fibrous nonwoven layer has a fibrous nonwoven layer comprises from 0.1 wt. % of the dry coating composition, as measured over the total coated area.

The lubricant may have an HLB which is within the range of from 6 to 18.

Hydrophilic-Lipophilic Balance

Griffin's method for non-ionic surfactants as described in 1954 works as follows:

$$HLB = 20 * M_h/M$$

where $M_h$ is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule.

The HLB value can be used to predict the surfactant properties of a molecule:

<10: Lipid-soluble (water-insoluble)
>10: Water-soluble (lipid-insoluble)
1 to 3: anti-foaming agent
3 to 6: W/O (water in oil) emulsifier
7 to 9: wetting and spreading agent
13 to 16: detergent
8 to 16: O/W (oil in water) emulsifier
16 to 18: solubilizer or hydrotrope Depending on the application method and the formulation that the lubricant agent is applied in prior to drying, the lubricant agent may be chosen based on the HLB value, such that if a water in oil emulsion is desired, a lubricant agent having an HLB value within the range of from 3 to 6 may be chosen. If the lubricant agent is applied in an aqueous solution, a lubricant agent having an HLB value above 10 is preferred.

The invention claimed is:

1. An absorbent article comprising a topsheet, the topsheet comprising a fibrous nonwoven layer arranged on a wearer facing side of the topsheet, wherein the fibrous nonwoven layer is coated over a coated area on the wearer facing side of the topsheet with a coating composition, the coating composition comprises a lubricant agent comprising an alkoxylated diester of myristyl alcohol and adipic acid, wherein the coating composition comprises one or more surfactants, and wherein the composition comprises from 50% by weight to 95% by weight of the lubricant agent and from 5% by weight to 50% by weight of the one or more surfactants.

2. The absorbent article according to claim 1, wherein the fibrous nonwoven layer consists essentially of thermoplastic fibers.

3. The absorbent article according to claim 1, wherein the lubricant has an HLB which is within the range of from 6 to 18.

4. The absorbent article according to claim 1, wherein the lubricant agent has a molecular weight of 500 g/mol or more.

5. The absorbent article according to claim 1, wherein the coating has a water content of greater than 0 wt. % and 0.5 wt. % or less.

6. The absorbent article according to claim 1, wherein the fibrous nonwoven layer comprises from 0.1 wt. % of the coating composition, as measured over the total coated area.

7. The absorbent article according to claim 1, wherein the coated area is at least 25% of the total surface area of the topsheet.

8. The absorbent article according to claim 1, wherein the topsheet in its transverse direction has a first and a second longitudinal side portion and an intermediate portion located between the first and the second longitudinal side portion, the first and the second longitudinal side portion each having a width of 30% of the width of the topsheet and the intermediate portion having a width of 40% of the topsheet, as measured at the widest point of the topsheet, and wherein the intermediate portion is continuously coated with the coating composition.

9. The absorbent article according to claim 1, wherein the absorbent article comprises a backsheet and an absorbent core arranged between the topsheet and the backsheet.

10. The absorbent article according to claim 9, wherein the coated area covers from 40% to 100% of the underlying absorbent core.

11. The absorbent article according to claim 9, wherein the absorbent core comprises pulp fibers.

12. The absorbent article according to claim 1, wherein the coating composition includes a buffering system.

13. The absorbent article according to claim 1, wherein the absorbent article comprises a front waist region and a rear waist region.

14. The absorbent article according to claim 1, wherein the absorbent article is an over-night absorbent article, a pant diaper, an open diaper, a belted absorbent article.

15. The absorbent article according to claim 1, wherein the absorbent article is an over-night absorbent article.

16. The absorbent article according to claim 1, wherein the one or more surfactants are selected from the group consisting of zwitterionic surfactants, cationic surfactants, anionic surfactants, and mixtures thereof.

17. The absorbent article according to claim 1, wherein the one or more surfactants are selected from the group consisting of cationic surfactants, anionic surfactants, and mixtures thereof.

* * * * *